US00PP10628P

United States Patent [19]

Olesen et al.

[11] Patent Number: Plant 10,628

[45] Date of Patent: Oct. 6, 1998

[54] MINIATURE ROSE PLANT NAMED 'POULFUNA'

[75] Inventors: L. Pernille Olesen; Mogens N. Olesen, both of Fredensborg, Denmark

[73] Assignee: Poulsen Roser ApS, Fredensborg, Denmark

[21] Appl. No.: 794,880

[22] Filed: Feb. 5, 1997

[51] Int. Cl.[6] ..... A01H 5/00

[52] U.S. Cl. ..... Plt./7.1

[58] Field of Search ..... Plt./7.1, 9

[56] References Cited

PUBLICATIONS

UPOV–ROM, 1997 Mar., Plant Variety Database, GTI Jouve Retrieval Software, two citations for 'POULfuna'.

*Primary Examiner*—Howard J. Locker

[57] ABSTRACT

A miniature rose plant with hot pink colored flowers which is extremely compact, floriferous, and which has good shelf life. The new variety propagates well by cuttings and is suited for the year-round production of flowering pot roses in glasshouses. The variety has shown to be uniform and stable in the resulting generations from such asexual propagation.

2 Drawing Sheets

SUMMARY OF THE DISCOVERY

The present discovery constitutes a new and distinct variety of miniature rose plant which was discovered in a cultivated area. The new variety is named 'POULfuna'.

The unique qualities that this variety has are:

1. Abundant clusters of hot pink flowers with good shelf life;

2. Extremely compact growth, thereby making the variety suitable for production in pot sizes of 6 cm in diameter;

3. Year round flowering under glasshouse conditions;

4. Suitable for production from softwood cuttings in pots;

5. Dark green foliage with excellent disease resistance.

This combination of qualities was not present in previously available commercial cultivars of this type and distinguish 'POULfuna' from all other varieties of which we are aware.

'POULfuna' was selected by L. Pernille and Mogens N. Olesen in a rose development program in Fredensborg, Denmark in March of 1993. The new rose variety resulted from a naturally occurring mutation of unknown causation discovered in a controlled planting as a branch of the rose variety 'POULtre' described and illustrated in U.S. Plant Pat. No. 9,021 and issued on Dec. 27, 1994. Poulsen Roser ApS, et al is the inventor of the rose variety 'POULtre', from which the new variety mutated.

Asexual reproduction of 'POULfuna' by cuttings was first done by L. Pernille and Mogens N. Olesen in April of 1993. This initial and subsequent propagations have demonstrated that the characteristics of 'POULfuna' are true to type and are transmitted from one generation to the next.

BRIEF DESCRIPTION OF THE DRAWINGS

The accompanying color illustrations show examples of the new variety's vegetative growth, buds, flowers, and stems in various stages of development.

Specifically illustrated in Sheet 1:

1. Stem showing branching and the attachment of leaves, buds, and flowers;

2. Flower bud, partially opened bud, and open bloom;

3. Flower petals, detached;

4. Sepals, receptacle, and pedicel;

5. Flowering stem with terminal and lateral buds, as well as a bare stem exhibiting thorns;

6. Leaves.

Specifically illustrated in Sheet 2 is an entire blooming plant in a pot.

DETAILED DESCRIPTION OF THE VARIETY

The following is a detailed description of 'POULfuna', as observed in its growth in greenhouses in Fredensborg, Denmark and Half Moon Bay, Calif., and in a field nursery in Applegate, Oreg. Descriptions were made from plants treated with growth regulators normally used in the greenhouse production process. The growth regulator Paclobutrazol was applied at 15 ppm weekly for three weeks beginning at a plant age of 6 weeks. The peduncle lengths mentioned may actually be shorter and the foliage color several shades darker than on untreated specimens. Color references are made using The Royal Horticultural Society (London, England) Colour Chart.

For a comparison, the nearest existing rose variety is 'POULtre', a patented variety described and illustrated in U.S. Plant Pat. No. 9,021 and issued on Dec. 27, 1994. Chart 1 details several physical characteristics of the presently disclosed and the comparison variety.

CHART 1

| Characteristic | 'POULfuna' | 'POULtre' |
|---|---|---|
| Flower bud | RHS 53D of the Red-Purple Group | RHS 49C of the Red Group |
| Flower bloom, upper surface of petals | RHS 57B of the Red-Purple Group | RHS 49C of the Red Group |

Mutation resulted from: 'POULtre' U.S. Plant Pat. No. 9,021 issued on Dec. 27, 1994.

Classification:

*Botanical.—Rosa hybrida.*

*Commercial.—Miniature.*

Flower

Blooming cycle: Recurrent.

Flower bud:

*Size.*—6 mm in diameter and 10–12 mm in height at cracked bud phase.

*Bud form.*—Pointed to ovoid.

*Bud color.*—R.H.S. 53 D of the Red-Purple Group, at ¼ opening.

*Sepals.*—Green, with weak foliaceous appendages. Covered with fine hairs.

*Peduncle.*—Surface: Smooth or nearly so. Length: Varies from 10–20 mm. Color: Medium green. Prickles: Few to none.

*Receptacle.*—Surface: Smooth. Glabrous. Shape: Pitcher shaped. Size: Small. 3 mm×3 mm. Color: R.H.S. 141 C of the Green Group.

*Borne.*—Multiple buds, with one to four buds per stem.

Flower bloom:

*Diameter.*—Small. 30–35 mm average diameter when open.

*Length.*—8–10 mm. average bud length from point of sepal attachment.

*Form.*—Upon opening, ovoid. Completely open flower is flat, with petals reflexing slightly.

*Petalage.*—Double. Average range: 30–35 petals per flower.

*Color.*—The upper side of the middle and the edge of the petal is R.H.S. 57 B, of the Red-Purple Group. The reverse side of the middle and edge of the petal is R.H.S. 57 D, of the Red-Purple Group. After opening, the upper surface fades only slightly to a R.H.S. 57 C, of the Red-Purple Group. A small spot of yellow, R.H.S. 2 C of the Yellow Group, exists at the base of the inside and the outside of the petal.

*Reflex.*—Petals reflex at or near the petal edge, with the outermost rows of petals double reflexed, forming a somewhat of a point.

*Petal edge.*—Petal edge lacks undulation.

*Fragrance.*—Very light to light.

*Duration.*—Very long lasting, 10–14 days on the plant.

Reproductive organs:

*Pollen.*—Limited. Light yellow. Yellow Group 13C.

*Anthers.*—Size: Small. Numerous. Color: Yellow. Yellow Group 13A.

*Filaments.*—Color: Light yellow. Green-Yellow Group 1C.

*Stigmas.*—Color: Yellow-green. Yellow-Green Group 154C. Positioned at the same level as the anthers.

*Styles.*—Medium in length, with stigmas above receptacle mouth. Style surface is weakly pubescent. Yellow-Green Group 149D.

*Ovaries.*—Inferior.

Plant

Plant growth: Extremely compact, vigorous, upright to bushy. When grown as a 6 cm pot plant, the average height of the plant itself is 8–10 cm and the average width is 8–10 cm. When grown as a nursery plant on its own roots the average plant height is 20–25 cm and the average plant width is 20–25 cm.

Stems:

*Color.*—Young wood: Green. Green Group 143B. Young stems show little or no anthocyanin coloration. Older wood: Green. Green Group 139B.

*Bark.*—Young wood: Smooth. Older wood: Smooth.

*Thorns.*—Incidence: Present. Concave to straight shaped. Size: Average length: 3 mm. Color: Red-brown to tan. Greyed-Orange Group 164C.

Plant foliage:

*Normal number of leaflets on average leaves.*—5 leaflets.

*Leaf size.*—Small. 50 mm×30 mm.

*Abundance.*—Average abundance.

*Color.*—Top: Dark green. Color group R.H.S. 147 A, of the Yellow-Green Group. Bottom: Medium green. Color group 147 C, of the Yellow-Green Group. Juvenile foliage: Medium green. The upper leaf surface is Yellow-Green Group 147A. The lower leaf surface is Yellow-Green Group 147C. Mature foliage: Medium green. Color group 144 A of the Yellow-Green Group. Mature foliage is paler in color than juvenile foliage.

Plant leaves and leaflets:

*Stipules.*—Present. Ave. 6 mm in length. Yellow-Green Group 147A.

*Petiole.*—Length: 12–15 mm. Underneath: With prickles. Color: Green Group 143B.

*Rachis.*—With prickles. Green. Green Group 143B.

*Edge.*—Serrated.

*Shape.*—Leaflets are ovate to acute.

*Leaflets.*—Number: Commonly 5.

*Texture.*—Upper side: Glossy and smooth.

*Other.*—Thin texture. Leaflets are flat.

Disease resistance: Resistant to blackspot, mildew, and rust under normal growing conditions.

We claim:

1. A new and distinct variety of rose plant of the miniature class, substantially as herein illustrated and described as a distinct and novel rose variety due to its abundant hot pink flowers, excellent keeping ability, suitability for forcing year-round, and extremely compact growth which limits the need for application of growth regulators in commercial culture.

* * * * *

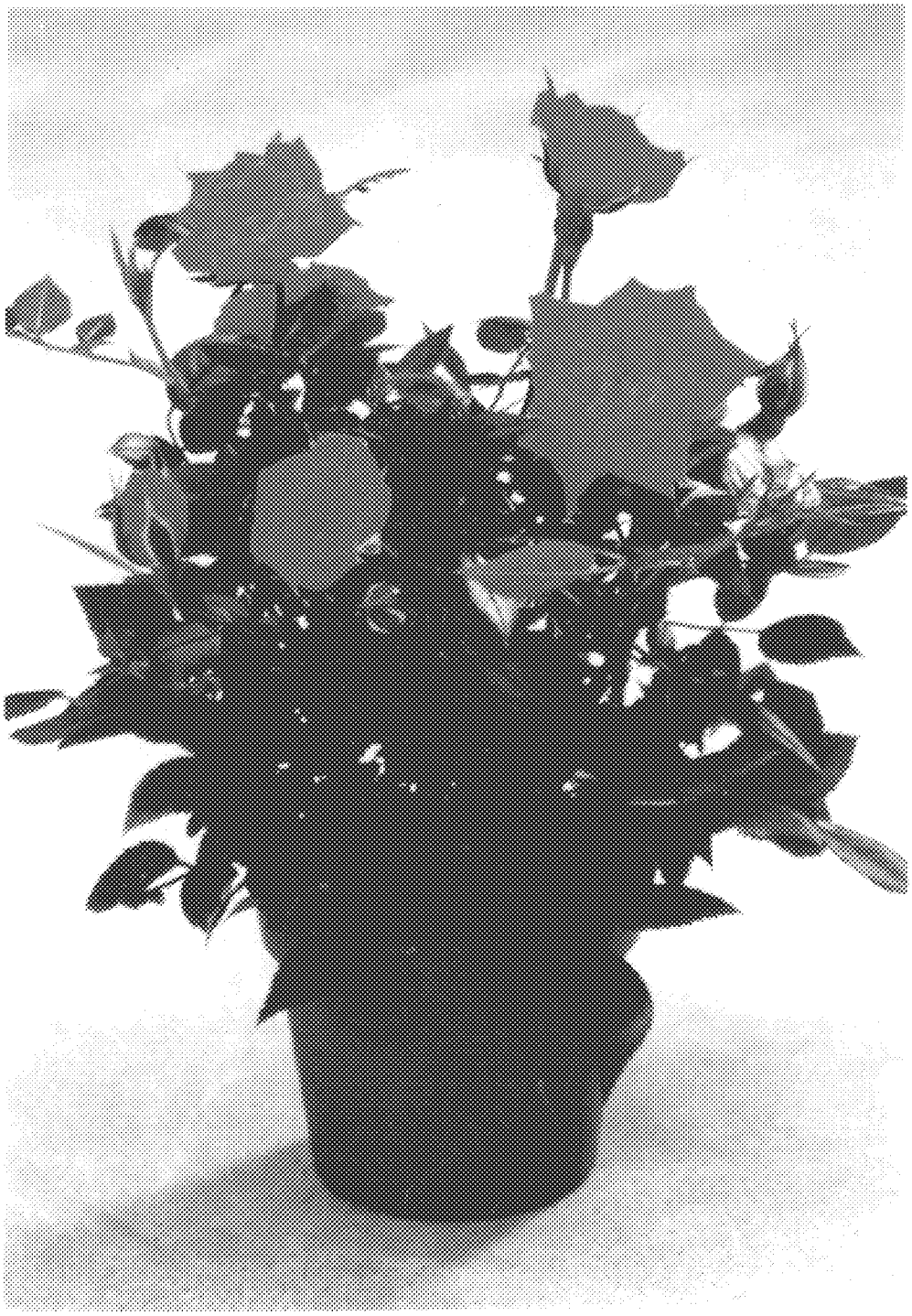

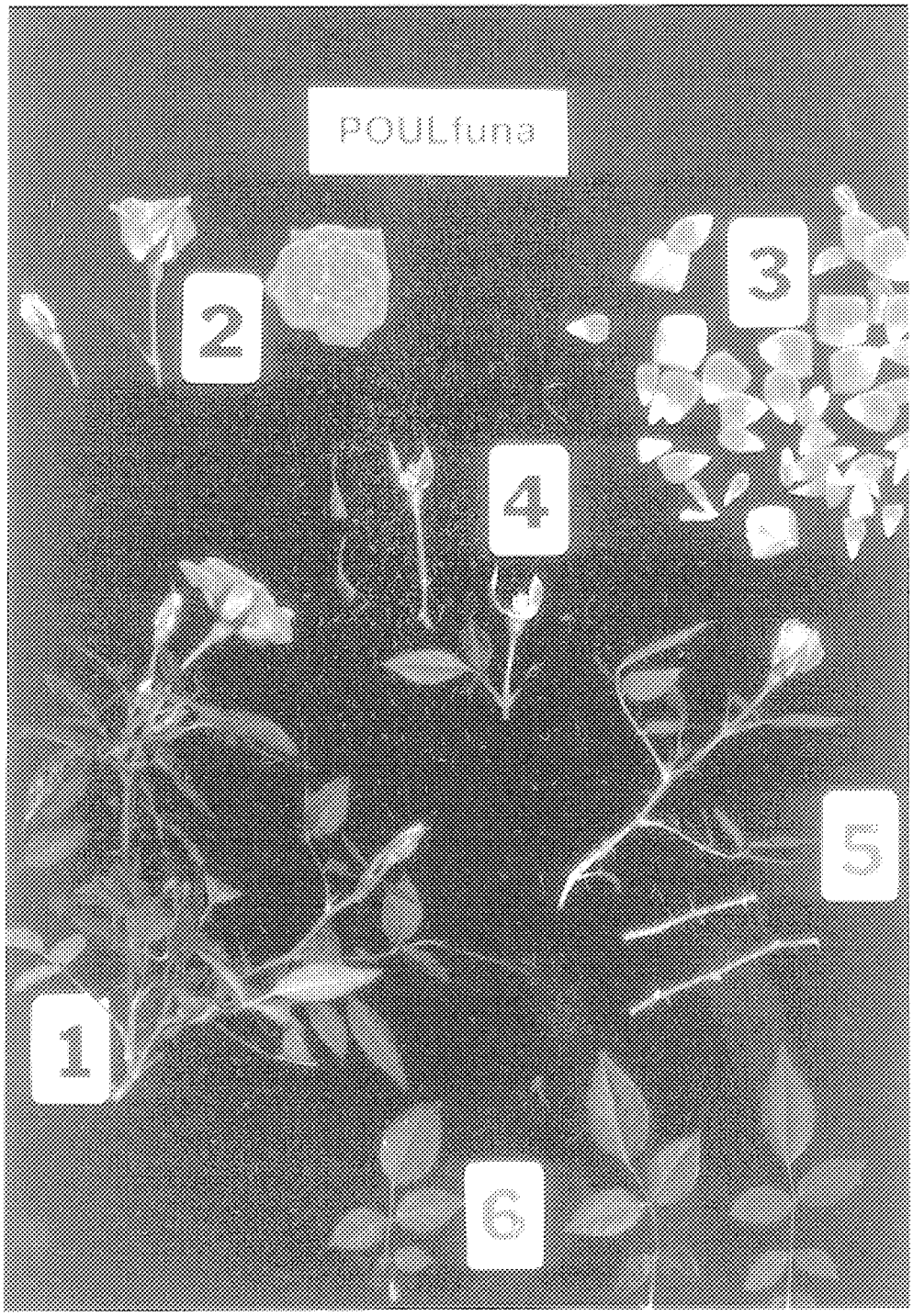
POULfuna
1
2
3
4
5
6